United States Patent [19]

Schoenwald et al.

[11] 4,271,143
[45] Jun. 2, 1981

[54] SUSTAINED RELEASE OPHTHALMIC DRUG DOSAGE

[75] Inventors: Ronald D. Schoenwald; Robert E. Roehrs, both of Fort Worth, Tex.

[73] Assignee: Alcon Laboratories, Inc., Fort Worth, Tex.

[21] Appl. No.: 37,314

[22] Filed: May 9, 1979

Related U.S. Application Data

[63] Continuation of Ser. No. 872,074, Jan. 25, 1978, abandoned.

[51] Int. Cl.³ ............... A61K 31/74; A61K 31/78; A61K 31/71; A61K 31/35
[52] U.S. Cl. .................................. 424/78; 424/81; 424/181; 424/273 R; 424/283; 424/300; 424/324; 424/331
[58] Field of Search .............. 424/78, 81, 181, 273 R, 424/283, 300, 324, 331

[56] References Cited

U.S. PATENT DOCUMENTS

| 2,707,777 | 3/1955 | Feinstein et al. | 424/148 |
| 2,798,053 | 7/1957 | Brown | 424/81 |
| 3,214,338 | 10/1965 | Ehrlich | 424/78 |
| 3,947,573 | 3/1976 | Rankin | 424/78 |
| 3,966,902 | 6/1976 | Chromecek | 424/78 |
| 4,003,991 | 1/1977 | Krohn et al. | 424/81 |

FOREIGN PATENT DOCUMENTS

2212392 9/1973 Fed. Rep. of Germany.
2173736 12/1973 France.

OTHER PUBLICATIONS

J. Pharm. Sciences 67(9), pp. 1280–1283, (1978), Schoenwald et al.

Primary Examiner—Douglas W. Robinson
Attorney, Agent, or Firm—Fitch, Even, Tabin, Flannery & Welsh

[57] ABSTRACT

The present invention is directed to an aqueous dispersion of an ophthalmic drug and a high molecular weight polymer which forms a highly viscous gel and can be used to prolong the duration of activity of the ophthalmic drug when the gel is applied into the conjunctival sac of the eye. The ophthalmic drug-containing gel composition has prolonged retention time in the eye and remains in contact with the surface of the eye for an extended period of time.

29 Claims, No Drawings

SUSTAINED RELEASE OPHTHALMIC DRUG DOSAGE

This application is a continuation of Ser. No. 872,074 filed Jan. 25, 1978, now abandoned.

The present invention relates generally to compositions and a method for treatment of a diseased eye. More particularly, the present invention is directed to the topical administration to the eye of a long-acting, well-retained gel preparation containing an ophthalmic drug.

Various ophthalmic drugs have been found to have therapeutic usefulness in treatment of diseases of the eye. Such ophthalmic drugs include pilocarpine, epinephrine, tetracycline, corticosteroids and carbachol. It has been a problem in the use of such ophthalmic drugs to retain the drug in contact with the surface of the eye for a sufficient period to accomplish the therapeutic purpose.

Various methods have been proposed to increase the time of contact of ophthalmic drugs with the eye. For example, U.S. Pat. No. 3,828,777 to Ness describes an ocular device for the controlled and continuous administration of a predetermined dosage of drug to the eye. The ocular device of the Ness patent is a body of microporous drug release-rate controlling material which is insoluble in tear fluid. The pores of the body are filled with a medium permeable to the passage of a drug by diffusion. The body further contains a reservoir of a drug formulation confined in the body which is of limited solubility in the medium and which is of a shape that is adapted for insertion and retention in the conjunctival sac. The body continuously meters the flow of a therapeutically effective amount of drug to the eye and surrounding tissues at a controlled rate over a long period of time.

Ocular insert devices are known and are intended for use in prolonging the effect of a drug contained within the ocular insert device. U.S. Pat. No. 3,811,444 to Teller et al, U.S. Pat. No. 3,826,258 to Abraham et al, and U.S. Pat. No. 3,786,812 to Neefe are directed to such devices. U.S. Pat. No. 3,845,201 to Haddad and U.S. Pat. No. 3,914,402 to Shell are directed to prior art solid drug dosage forms. Previously known ointments containing drugs have not been effective in that they are not clear and therefore form a barrier to sight or in that they are rapidly removed by the normal function of the eye and the prolonged rate of release of the drug is not attained. U.S. Pat. No. 4,003,991 to Krohn et al is directed to an ophthalmic ointment having a relatively low viscosity which includes a water soluble polymer and a therapeutic agent.

Accordingly, it is a principal object of the present invention to provide a composition and method for treating a diseased eye.

It is another object of the present invention to provide a composition and method for topical application to an eye which provides a long-acting, well-retained gel preparation containing an ophthalmic drug.

It is a further object of the present invention to provide a composition and method for treatment of a diseased eye wherein an ophthalmic drug is reacted with a polymer to provide a complex and/or salt suitable for topical application to an eye wherein the ophthalmic drug is slowly released from the complex and/or salt.

These and other objects of the invention will become more apparent from the following detailed description and the accompanying claims.

Generally, the present invention is directed to an aqueous dispersion of an ophthalmic drug and a high molecular weight polymer which forms highly viscous gels and can be used to prolong the duration of activity of the ophthalmic drug when the gel is applied into the conjunctival sac of the eye. The prolongation of activity of the ophthalmic drug is accomplished through slow release of the drug from the gel matrix and/or a slow erosion of gel surface. The drug containing gel compositions of the present invention have a prolonged retention time in the eye and remain in contact with the surface of the eye for an extended period of time.

The high molecular weight polymers useful in the present invention have a molecular weight of from about 1 million to about 6 million. The polymers are characterized as having carboxylic or anhydride functional groups and preferably contains from 2 to 7 carbon atoms per functional group. The gels which form during the preparation of the ophthalmic drug/polymer dispersion have a viscosity of from about 40,000 to about 300,000 cps at 20 rpm (spindle 7) at 25° C. generated by an RVT Brookfield Viscometer, preferably from about 75,000 to about 20,000 cps. The viscosity of the gels is too high to be measured with a No. 3 spindle. The gels further are characterized as having a yield value of from about 5,000 to about 20,000 dyne/cm$^2$ or more as determined by a Ferranti-Shirley Viscometer at 25° C.

The high molecular weight polymers used in the compositions of the present invention not only thicken the compositions to provide a gel, but they also provide a special type of viscosity or rheology i.e., plastic viscosity. Plastic viscosity is indicative of a material that does not flow until a certain force or stress value is exceeded. This is referred to as the yield value. While not wishing to be bound by any theory, it is believed that the increased duration of activity of the ophthalmic drug in the gel compositions of the invention is related not only to the apparent viscosity (thickness), but is also related to the yield value. The gel compositions of the present invention also exhibit the rheological parameter of thixotropy which is related to the break down and rebuilding of the gel structure. As the gel compositions are sheared above the yield value and begin to flow, the structure is broken down; but when the shear is removed the structure reforms and may even reach the initial high viscosity and yield value.

The high molecular weight polymers useful in the ophthalmic compositions of the present invention are those which are capable of providing the rheological characteristics of high viscosity and high yield value at the levels set forth herein above.

Suitable polymers useful in the present invention are carboxypolymethylene, a carboxy vinyl polymer, (available under the trade name Carbopol from the B. F. Goodrich Company); and ethylene maleic anhydride, (available under the trade name EMA from the Monsanto Company). The polymers are used in the gel compositions at a level of from about 2 to about 8 percent by weight.

The compositions and method of the invention are adaptable for use with any of the ophthalmically active drugs, particularly amine drugs known for use in the treatment of diseases of the eye. These ophthalmic drugs include pilocarpine, epinephrine, tetracycline, phenylephrine, eserine, phospholine iodide, demecarium bromide, cyclopentolate, homatropine, scopolamine, chlortetracycline, bacitracin, neomycin, polymixin, gramicidin, oxytetracycline, chloramphenicol, gentamycin, penicillin, erythromycin, carbachol, sulfacetamide, polymixin B, idoxuridine, isoflorophate, fluoromethalone, dexamethasone, hydrocortisone, hydrocortisone acetate, dexamethasone 21-phosphate, fluorocinolone, medrysone, prednisolone, methyl prednisolone, prednisolone 21-phosphate, prednisolone acetate, betamethasone and triamcinolone.

The ophthalmic drug is present in the gel compositions at a level effective to accomplish the purpose of the drug. Usual levels of use of the ophthalmic drug are in the range of from about 0.03 to about 15 percent by weight of the gel composition.

The invention is particularly suitable for prolonging the activity of pilocarpine, which has been a goal in ophthalmic treatment of the eye for a long time. Accordingly, various aspects of the invention are hereinafter particularly described with reference to the use of pilocarpine as the ophthalmic drug in compositions of the invention.

Several methods have been used to prepare the drug/polymer compositions of the invention. One method, referred to herein as Method A, involves dispersing the polymer in water followed by the addition of a basic ophthalmic drug so as to neutralize the polymer. The neutralization is responsible for the formation of a hydrogel complex of the ophthalmic drug and polymer. The final pH is dependent upon the basicity of the ophthalmic drug and the amount added. If the drug is not sufficiently basic, the pH of the hydrogel can be adjusted by adding a basic material, such as ammonium hydroxide, sodium hydroxide, ethanolamine or other basic compounds to provide a desired pH. It is preferred to provide a pH of from about 4.5 to about 8.5 in the ophthalmic drug/polymer gel formulations. It has also been determined that any ophthalmic drug can be added to a hydrogel formed by addition of a basic (non-drug) agent to the polymer to first form the gel, followed by addition of the ophthalmic drug in any desired concentration.

In a second method, referred to herein as Method B, a salt of an ophthalmic drug and the polymer is prepared. The ophthalmic drug salt is prepared by dispersing the polymer in an inert organic solvent, such as hexane, benzene or chloroform, to form a slurry. Thereafter, a solution of the ophthalmic drug in the solvent is added to the slurry. An acid-base neutralization reaction takes place in which the polymer-ophthalmic drug product precipitates from the solvent. After removal of the solvent, a finely divided powdered solid remains. For some ophthalmic drugs, such as carbachol, a solid mass is produced by the neutralization reaction. The solid mass can be reduced to fine particles by grinding. Thereafter, a gel is prepared by dispersion of the finely divided powdered product in water.

A third method referred to herein as Method C, utilizes the acid salt form of the drug. A non-drug base, such as sodium hydroxide is used to neutralize an aqueous dispersion of the polymer and form a gel followed by addition of the acid salt form of the drug.

The duration of activity of gel formulations containing an ophthalmic drug prepared by all three methods described herein is at least twice the duration of commercial ophthalmic drug preparations. A study of pilocarpine formulations complexed with carboxypolymethylene by the Method A procedure indicates that these gel formulations are unique in that they remain in the conjunctival sac of a rabbit for a period of 4 to 8 hours. Prior art formulations, such as petrolatum salves or suspensions of slightly soluble salts of pilocarpine have been found to be flushed from the rabbit eye in a period of 15 to 30 minutes.

In a further embodiment of the present invention finely divided particles of an ophthalmic drug salt of the polymer prepared in accordance with Method B is suspended in a non-aqueous vehicle, such as stabilized oil, e.g. mineral oil, vegetable oil and silicone fluid. Thereafter, the suspended particles are administered directly into the eye. A gel immediately forms with the eye by reaction of the particles with the tears of the eye. Pilocarpine salts of carboxypolymethylene containing 2 mg of pilocarpine per dose have yielded miosis durations of 14 hours in rabbit eyes, whereas, aqueous solutions of pilocarpine have miosis durations of only 4 to 6 hours.

In a still further embodiment the ophthalmic drug salt particles can be placed directly in the eye by any suitable means. The particles then gel in situ in the eye by reaction with the tears of the eye.

The following examples further illustrate various features of the invention, but are intended to no way limit the scope of the invention which is set forth in the appended claims.

EXAMPLE I

A salt form of carboxypolymethylene and pilocarpine is prepared by Method B, six grams of carboxypolymethylene (available under the trade name Carbopol 940 from B. F. Goodrich Co.) is stirred into 30 ml of hexane. Four grams of pilocarpine is dissolved in 30 ml of hexane. The pilocarpine solution is then blended with the suspension of carboxypolymethylene. An acid-base neutralization reaction occurs to form a salt of pilocarpine and carboxymethylene. The salt form of carboxymethylene and pilocarpine is recovered from the hexane carrier in the form of a finely divided powder containing about 35 to 40 percent by weight of pilocarpine.

Two gel formulations are prepared containing the pilocarpine/carboxypolymethylene salt. The gel formulations contain the ingredients indicated hereinbelow in Table I at the indicated level.

TABLE I

| | % by weight | |
|---|---|---|
| Ingredient | Formulation A | Formulation B |
| Carboxypolymethylene/ Pilocarpine Salt | 5.15 | 5.15 |
| Benzalkonium Chloride (U.S.P.) | 0.01 | 0.01 |
| Sodium Hydroxide (3N) | qs-pH 5.35 | qs-pH 6.0 |
| Purified Water | qs 100 | qs 100 |

The procedure for obtaining 100 gram of finished gel consists of adding Benzalkonium Chloride to 80 gram of purified water. The benzalkonium chloride solution is stirred as the salt form powder of carboxypolymethylene/pilocarpine is quickly added. The solution is vigorously stirred so as to wet as much of the salt form powder as possible before the gel forms in about one to two minutes. Stirring is continued until there is no further apparent hydration. Sufficient sodium hydroxide is then added incrementally to provide the indicated pH.

Purified water is then stirred into the gel to bring the final gel weight to 100 gram. The gel preparation is autoclaved at 120° C. for 20 minutes followed by fast exhaust. The finished gel may contain air bubbles which can be removed by centrifugation.

Using the Ferranti-Shirley Viscometer under the following conditions: 3X Switch Position, 60 seconds sweep, medium cone and 100 rpm spring constant, the following viscosity determinations are obtained:

TABLE II

|  | A 25° C. | A 37° C. | B 25° C. | B 37° C. |
|---|---|---|---|---|
| Plastic Viscosity (CPS) | 740 | 708 | 546 | 804 |
| Yield Value (DYNE/CM$^2$) | 11421 | 10778 | 13351 | 11421 |

Human miosis data is obtained by placing 50 microliter doses of formulation A and B into the left eye of nine healthy human volunteers. The untreated right eye serves as the control. Formulations A and B and the control formulation of a standard pilocarpine solution contain the equivalent of 2 percent pilocarpine by weight. The following data is obtained.

TABLE III

| | Treated pupil diameter minus control pupil diameter. | | |
|---|---|---|---|
| Time (hr) | A | B | Control 2% Pilocarpine Solution |
| | Pupil Diameter Differences (mm) | | |
| 1 | 2.42 | 2.33 | 2.50 |
| 3 | 2.44 | 2.56 | 1.83 |
| 6 | 2.56 | 2.44 | 1.19 |
| 9 | 1.81 | 1.89 | 0.72 |
| 12 | 1.39 | 1.17 | 0.64 |
| 24 | 0.17 | 0.06 | −0.19 |

The larger pupil diameter differences following 1 hour for gel compositions A and B compared to the control illustrate the longer duration of the gel compositions of the invention.

EXAMPLE II

Three additional formulations are prepared and used to determine rabbit miosis data. The formulations contain the indicated ingredients at the levels indicated below:

TABLE IV

| | Formulations | | |
|---|---|---|---|
| Ingredients | A | B | C |
| Pilocarpine HCl, U.S.P. | 2.0 grams | — | — |
| Pilocarpine Carboxypolymethylene/Pilocarpine Salt | — | 1.7 grams | — |
| Carboxypolymethylene) Carbopol 940 from B. F. Goodrich Co.) | — | — | 5.15 grams |
| Benzalkonium Chloride (U.S.P.) | 3.38 grams | 3.38 grams | — |
| Sodium Hydroxide, 3N | 0.01 grams | 0.01 grams | 0.01 grams |
| Purified Water | qs pH 5.4 qs 100 grams | qs pH 5.4 qs 100 grams | qs pH 5.4 qs 100 grams |

Formulation C of Table IV is prepared as set forth hereinabove under Example I and is identical to Formulation A of Example I.

Formulation A of Table IV is prepared as follows: Pilocarpine HCl and Benzalkonium Chloride are dissolved in 80 grams of purified water. While vigorously stirring this solution, carboxypolymethylene is slowly added to the vortex. Agitation is continued until a cloudy solution without lumps is attained.

After stirring is stopped, the entrapped air is allowed to escape. A 10 gram solution containing about 95 percent of the molar requirement of sodium hydroxide is slowly added to the cloudy solution with stirring. A gel rapidly forms as stirring is continued for 10 to 20 minutes. The gel is stored overnight under refrigeration to complete the hydration and allow the pH to come to equilibrium. The final pH of the finished gel is adjusted by adding 3 N Sodium Hydroxide dropwise, and mixing well with each incremental addition. Purified water is then stirred into the gel to bring the gel weight up to the final weight of 100 gram. If the finished gel contains air bubbles, they are removed by centrifugation.

Formulation B of Table IV is prepared as follows: Benzalkonium Chloride is dissolved in 80 gram of purified water. While vigorously stirring this solution, carboxypolymethylene is slowly added to the vortex. Agitation is continued until a cloudy suspension without lumps is attained. After stirring is stopped, entrapped air is allowed to escape. A 10 gram solution containing pilocarpine is prepared and is slowly added to the carboxypolymethylene solution with stirring. A gel rapidly forms. Stirring is continued for 10 to 20 minutes. The pH of the gel is brought to within 0.1 to 0.2 pH of the desired pH by the addition of 3 N Sodium Hydroxide, mixing well after each incremental addition of sodium hydroxide. The gel is stored overnight under refrigeration to allow the pH to come to equilibrium. The final pH is adjusted to 5.4 and purified water is added to the gel to bring its weight up to the final weight of 100 grams. If the finished gel contains air bubbles they are removed by centrifugation.

The final pH of Formulation A and Formulation B is measured and found to be 5.35. A rheograph is generated using a Ferranti-Shirley Viscometer under the following condition: 2X Switch position, 60 seconds sweep, medium cone and 100 rpm spring constant. The viscosity determinations obtained are:

TABLE V

| | Formulation | |
|---|---|---|
| | A (37° C.) | B (37° C.) |
| Plastic Viscosity (CPS) | 784 | 910 |
| Yield Value (DYNE/CM$^2$) | 11480 | 14560 |

Miosis-Time Data using 6 albino rabbits is obtained for the various formulations of Table IV and a control formulation of a pilocarpine solution as described hereinabove in Example I. The miosis data is set forth hereinbelow in Table VI.

TABLE VI

| | Pupil Diameter (mm) | | | Control 2% Pilocarpine |
|---|---|---|---|---|
| Time (Hr) | A | B | D | Solution |
| 0 | 5.29 | 5.35 | 5.18 | — |
| 0.5 | 3.46 | 3.43 | 3.62 | 3.21 |
| 1.0 | 3.44 | 3.40 | 3.46 | 3.42 |

TABLE VI-continued

| Time (Hr) | Pupil Diameter (mm) A | B | D | Control 2% Pilocarpine Solution |
|---|---|---|---|---|
| 2.5 | 3.22 | 3.46 | 3.60 | 4.20 |
| 3.5 | 3.61 | 3.56 | 3.77 | 4.66 |
| 4.5 | 3.85 | 3.72 | 4.04 | 5.32 |
| 5.5 | 4.35 | 4.33 | 4.08 | — |
| 7.5 | 4.79 | 5.08 | 4.69 | — |
| 8.5 | 5.02 | 4.57 | 4.54 | — |
| 9.5 | 5.15 | 4.90 | 4.70 | — |
| 10.5 | — | 5.0 | 4.65 | — |
| 11.5 | — | 5.1 | 5.25 | — |

The topically applied ophthalmic gel compositions of the invention provide a therapeutic composition with prolonged retention and slow drug release which can be used for various diseased conditions of the eye, particularly glaucoma when the active agent is pilocarpine, epinephrine or carbachol. The known prior art ophthalmic compositions with slow releasing properties are either solid inserts, flakes of various compositions and design, or suspensions which are steroid preparations or ointment dosage forms. The ointment dosage forms primarily contain petrolatum and small quantities of lanolin or its derivatives. A further known ointment dosage form consists of polyethylene containing liquid petrolatum trapped within its matrix. The prior art ointment dosage forms are substantially oleaginous and are not cosmetically appealing since they are greasy and blur the vision. In addition they have been found to prolong therapeutic or pharmalogical activity by approximately 25 percent at best compared to aqueous preparations, whereas the ophthalmic drug/polymer gel compositions in the present invention have prolonged activity two to three times when compared to aqueous solutions. Moreover, the gel compositions of the present invention contain about 95 percent by weight of water trapped within the polymer matrix and are not greasy, are clear so that the vision is not blurred and their refractive index is similar to that of tears.

EXAMPLE III

In accordance with method C, the acid salt form of pilocarpine is incorporated within a gel made from ethylene maleic anhydride (available under the trade name of EMA-91 from Monsanto). Two gel preparations are prepared and contain the ingredients indicated herein below in Table VII.

TABLE VII

| Ingredient | % by weight Formulation A | Formulation B |
|---|---|---|
| Ethylene maleic anhydride | 3.38 | 5.0 |
| Pilocarpine hydrochloride (U.S.P.) | 1.90 | 2.0 |
| 28% ammonium hydroxide | 2.27 | 3.5 |
| Mannitol, N.F. | 1.9 | 2.0 |
| Benalkonium chloride (U.S.P.) | 0.01 | 0.01 |
| Purified water | qs | qs |

The procedure for preparing 100 grams of finished gel consists of adding ethylene maleic anhydride to the vortex of 25 ml of vigorously stirred water using a high speed mixer. One minute of mixing was sufficient in order to completely wet and disperse the polymer. Ammonium hydroxide was added to the dispersion and mixed for one or two minutes until a rigid gel was formed. Pilocarpine hydrochloride, mannitol and benzalkonium chloride were dissolved in 15 ml of purified water and added to the gel. This mixture is stirred for 4 minutes. A pH reading of 5.1 is obtained.

Using a Brookfield RVT Viscometer at 20 rpm equipped with spindle #7, and also using a Ferranti-Shirley Viscometer under the following conditions; 3X switch position, 60 second sweep, medium cone and 100 rpm spring constant, the following viscosity determinations are obtained:

TABLE VIII

| | A | | |
|---|---|---|---|
| | 24° C. | 25° C. | 37° C. |
| Brookfield Viscosity (cps) | 123,000 | — | — |
| Ferranti-Shirley Plastic Viscosity (cps) | — | 434 | 384 |
| Ferranti-Shirley Yield Value (dynes/cm$^2$) | — | 7,614 | 7,077 |

| | B | | |
|---|---|---|---|
| | 24° C. | 25° C. | 37° C. |
| Brookfield Viscosity (cps) | 109,000 | — | — |
| Ferranti-Shirley Plastic Viscosity (cps) | — | 692 | 558 |
| Ferranti-Shirley Yield Value (dynes/cm$^2$) | — | 10,081 | 11,046 |

Miosis-time data using 6 albino rabbits is obtained from formulations A and B of Table VII and a control formulation of a pilocarpine hydrochloride aqueous solution. The miosis data is set forth herein below in Table IX. Fifty microliter doses were given.

TABLE IX

| Time (Hr) | Pupil Diameter (mm) A | B | Control 2% Pilocarpine Solution |
|---|---|---|---|
| 0 | 4.92 | 5.06 | 5.08 |
| 0.5 | 3.72 | 3.53 | 3.43 |
| 1.0 | 3.23 | 3.27 | 3.55 |
| 2.0 | 3.37 | 3.32 | 4.05 |
| 3.0 | 3.57 | 3.13 | 4.63 |
| 3.5 | 3.55 | 3.38 | 4.73 |
| 4.5 | 3.67 | 3.58 | 4.98 |
| 5.5 | 3.77 | 3.77 | 5.20 |
| 6.5 | 4.00 | 4.03 | — |
| 7.5 | 4.47 | 4.12 | — |
| 8.5 | 4.57 | 4.40 | — |
| 9.5 | — | 4.78 | — |
| 10.5 | — | 5.12 | — |

EXAMPLE IV

To demonstrate the dependency of ocular retention time on the enhanced duration of the gel compositions of the invention, two studies were conducted and summarized as follows:

a. Three groups of rabbits, six to a group, were dosed with 50 µl of carboxypolymethylene gel containing 1.7% pilocarpine prepared by method B. Using a saline saturated cotton swab, the gel was removed from two groups of rabbit eyes 60 and 120 minutes post instillation and compared to the control group in which the gel formulation remained in the rabbit eye. The control group of rabbits gave a miosis duration of 8.06 hours; whereas the test groups showed durations of 5.18 and 5.28 hours corresponding to removal of gel at 60 and 120 minutes post instillation. Therefore, removal of the gel from rabbit eyes, even after two hours, significantly shortened the duration of response.

b. Tritiated pilocarpine was used to prepare a carboxypolymethylene pilocarpine salt according to method B. Tritiated pilocarpine was also incorporated into petrolatum. Each formulation, containing 1.7% pilocarpine, was dosed in a volume of 50 μl to the right eye of rabbits. Periodically, a group of rabbits, six to a group, were sacrificed. The entire conjunctival sac of each rabbit was excised and the contents of tritiated pilocarpine determined in each. At two hours post instillation 30% of the pilocarpine/carboxypolymethylene formulation remained in the rabbit eye; however, the pilocarpine/petrolatum formulation remaining in the rabbit eye was reduced to 30% at only 15 minutes post instillation. Over 60% of the pilocarpine/petrolatum formulation was removed after five minutes; whereas, no pilocarpine/carboxypolymethylene had been removed at this same time period. The retention of the gel formulation was shown to be superior in rabbit eye retention to petrolatum which according to Fraunfelder and Hanna (Survey of Ophth., 18, 292, [1974]) is retained better than vehicles containing methylcellulose or polyvinyl alcohol. The pilocarpine was used partially as a convenient tracer in this study and the retention results could be qualitatively applied to other ophthalmic drugs as well.

What is claimed is:

1. An ophthalmic dosage of an aqueous gel for application to the conjunctival sac of the eye, said gel comprising an ophthalmic drug and a gel-forming high molecular weight carboxy vinyl polymer, said polymer having a molecular weight in excess of 1,000,000, said ophthalmic drug being present at a level of from about 0.03 to about 15 percent by weight, said polymer being present at a level of from about 2 to about 8 percent by weight, said gel having a viscosity of from about 40,000 to about 300,000 cps and a yield value of from about 5,000 to about 20,000 dyne/cm$^2$.

2. An aqueous gel in accordance with claim 1 wherein said polymer has a molecular weight of from about 1,000,000 to about 6,000,000.

3. An aqueous gel in accordance with claim 1 wherein said gel has a viscosity of from about 75,000 to about 200,000 cps.

4. An aqueous gel in accordance with claim 1 wherein said gel has a viscosity of from about 90,000 to about 150,000 cps.

5. An aqueous gel in accordance with claim 1 wherein said ophthalmic drug is selected from the group consisting of idoxuridine, pilocarpine and its acceptable salts, and carbachol.

6. An aqueous gel in accordance with claim 1 wherein said ophthalmic drug is an ophthalmic steroid selected from the group consisting of hydrocortisone, hydrocortisone acetate, dexamethasone, dexamethasone 21-phosphate, fluorocinolone, medrysone, prednisolone, methylprednisolone, prednisolone 21-phosphate, prednisolone acetate, fluorometholone, betamethasone and triamcinolone.

7. An aqueous gel in accordance with claim 1 wherein said ophthalmic drug is an ophthalmic antibiotic selected from the group consisting of neomycin, polymyxin, chloramphenicol, erythromycin, tobramycin and gentamycin.

8. An aqueous gel in accordance with claim 1 wherein the pH of said gel is from about 4.5 to about 8.5.

9. An aqueous gel in accordance with claim 1 wherein said ophthalmic drug is pilocarpine and said high molecular weight polymer is carboxy vinyl polymer, said gel having a viscosity of from about 75,000 to about 200,000 cps and a yield value of from about 5,000 to about 20,000 dyne/cm$^2$.

10. An improved method for delivering an ophthalmic drug to the surface of the eye over extended periods of time, comprising preparing an aqueous gel of an ophthalmic drug and a gel-forming high molecular weight carboxy vinyl polymer having a molecular weight in excess of 1,000,000, and adjusting the pH of said gel to between about 4.5 and about 8.5, said gel containing between about 0.03 and about 15 percent by weight of said ophthalmic drug and between about 2 and about 8 percent by weight of said polymer, said gel having a viscosity of between about 40,000 and about 300,000 cps and a yield point of between about 5,000 and about 20,000 dynes/cm$^2$, and introducing said gel into the conjunctival sac of the eye, whereby prolonged retention and slow release of said ophthalmic drug is provided.

11. A method in accordance with claim 10 wherein said polymer has a molecular weight of from about 1,000,000 to about 6,000,000.

12. A method in accordance with claim 10 wherein said aqueous gel has a viscosity of from about 75,000 to about 200,000 cps.

13. A method in accordance with claim 10 wherein said gel has a viscosity of from about 90,000 to about 150,000 cps.

14. A method in accordance with claim 10 wherein said ophthalmic drug is selected from the group consisting of idoxuridine, pilocarpine and its acceptable salts, and carbachol.

15. A method in accordance with claim 10 wherein said ophthalmic drug is an ophthalmic steroid selected from the group consisting of hydrocortisone, hydrocortisone acetate, dexamethasone, dexamethasone 21-phosphate, fluorocinolone, medrysone, prednisolone, methylprednisolone, prednisolone 21-phosphate, prednisolone acetate, fluorometholone, betamethasone and triamcinolone.

16. A method in accordance with claim 10 wherein said ophthalmic drug is an ophthalmic antibiotic selected from the group consisting of neomycin, polymyxin, chloramphenicol, erythromycin, tobramycin and gentamycin.

17. A method in accordance with claim 10 wherein the pH of said gel is from about 4.5 to about 8.5.

18. A method in accordance with claim 10 wherein said ophthalmic drug is pilocarpine and said high molecular weight polymer is carboxy vinyl polymer, said gel having a viscosity of from about 75,000 to about 200,000 cps and a yield value of from about 5,000 to about 20,000 dyne/cm$^2$.

19. An ophthalmic drug dosage comprising an anhydrous mixture of an ophthalmic drug and a gel-forming high molecular weight carboxy vinyl polymer having a molecular weight in excess of 1,000,000, the concentration of said ophthalmic drug and said polymer in said mixture being selected such that when said mixture is introduced into the conjunctival sac of the eye and mixed with the aqueous tear fluid therein an aqueous gel is formed containing between about 0.03 and about 15 percent by weight of said ophthalmic drug and between about 2 and about 8 percent by weight of said polymer, said gel having a viscosity of between about 40,000 and about 300,000 cps and a yield point of between about 5,000 and about 20,000 dynes/cm$^2$.

20. An ophthalmic dosage in accordance with claim 19 wherein said polymer has a molecular weight of from about 1,000,000 to about 6,000,000.

21. An ophthalmic dosage in accordance with claim 19 wherein said ophthalmic drug is selected from the group consisting of idoxuridine, pilocarpine and carbachol.

22. An ophthalmic dosage in accordance with claim 19 wherein said ophthalmic drug is an ophthalmic antibiotic selected from the group consisting of neomycin, polymyxin, chloramphenicol, erythromycin, tobramycin and gentamycin.

23. An ophthalmic dosage in accordance with claim 19, wherein said ophthalmic drug is pilocarpine and said high molecular weight polymer is carboxy vinyl polymer.

24. An ophthalmic dosage in accordance with claim 19 wherein said mixture is suspended in a non-aqueous vehicle.

25. A method in accordance with claim 19 wherein said vehicle is a stabilized oil selected from the group consisting of mineral oil, vegetable oil and silicone fluid.

26. An improved method for delivering an ophthalmic drug to the surface of the eye over extended periods of time, comprising preparing an anhydrous mixture of an ophthalmic drug and a gel-forming high molecular weight carboxy vinyl polymer having a molecular weight in excess of 1,000,000, introducing said mixture into the conjunctival sac of the eye and reacting said polymer with the aqueous tear fluid in said sac to form a gel containing between about 0.03 and about 15 percent by weight of said drug and between about 2 and about 8 percent by weight of said polymer, said gel having a viscosity of between about 40,000 and about 300,000 cps and a yield point of between 5,000 and 20,000 dynes/cm$^2$.

27. A method in accordance with claim 26 wherein said ophthalmic drug is selected from the group consisting of idoxuridine, pilocarpine and carbachol.

28. A method in accordance with claim 26 wherein said ophthalmic drug is an ophthalmic antibiotic selected from the group consisting of neomycin, polymyxin, chloramphenicol, erythromycin, tobramycin and gentamycin.

29. A method in accordance with claim 26 wherein said ophthalmic drug is pilocarpine and said high molecular weight polymer is carboxy vinyl polymer.

* * * * *

UNITED STATES PATENT AND TRADEMARK OFFICE
CERTIFICATE OF CORRECTION

PATENT NO. : 4,271,143
DATED : June 2, 1981
INVENTOR(S) : Ronald D. Schoenwald and Robert E. Roehrs It is certified that error appears in the above—identified patent and that said Letters Patent is hereby corrected as shown below:

Column 2, line 26, "20,000 cps" should be --200,000 cps--

Column 6, line 66, Table VI, "D" should be --C--

Column 7, line 5, Table VI continued, "D" should be --C--

Column 11, line 20, Claim 25, "A method" should be --An ophthalmic drug dosage--

Signed and Sealed this

Twenty-ninth Day of September 1981

[SEAL]

Attest:

GERALD J. MOSSINGHOFF

Attesting Officer

Commissioner of Patents and Trademarks